United States Patent [19]

Kees, Jr.

[11] Patent Number: 4,796,625
[45] Date of Patent: Jan. 10, 1989

[54] ANEURYSM CLIP

[75] Inventor: George Kees, Jr., Alexandria, Ky.

[73] Assignee: Codman & Shurtleff, Inc., Randolph, Mass.

[21] Appl. No.: 441,535

[22] Filed: Nov. 15, 1982

[51] Int. Cl.$^4$ ............................................. A61B 17/12
[52] U.S. Cl. .................................. 128/325; 128/346; 24/552
[58] Field of Search ............... 128/346, 325, 321, 354; 81/43; 24/551, 552, 549, 553, 554

[56] References Cited

U.S. PATENT DOCUMENTS

| | | | |
|---|---|---|---|
| 450,266 | 4/1891 | Truax | 128/346 |
| 619,949 | 2/1899 | Flynn | 294/99 X |
| 1,133,334 | 3/1915 | Strycker | 294/99 X |
| 1,837,277 | 12/1931 | Lund | 128/321 |
| 2,215,725 | 9/1940 | Martinson | 128/346 X |
| 2,583,020 | 1/1952 | Smith | 16/87.2 X |
| 3,827,438 | 8/1974 | Kees | 128/325 X |
| 4,360,023 | 11/1982 | Sugita et al. | 128/325 |

Primary Examiner—Michael H. Thaler
Attorney, Agent, or Firm—Paul A. Coletti

[57] ABSTRACT

A one-piece aneurysm clip having an elongated flat ribbon body. The body includes a central helical portion joining first connecting portions, second connecting portions extending from the first connecting portions transversely of the first connecting portions and blade portions extending from the second connecting portions. Spring action of the helical portion urges the blade portions to substantially flatwise engaged position. A guide bar and stop member is mounted on one of the second connecting portions and has a guide bar position which overlies an opposed other of the second connecting portions to hold the blade portions in alignment. A stop portion of the guide bar and stop member is engageable by the other of the second connecting portions to limit opening of the clip.

1 Claim, 1 Drawing Sheet

ANEURYSM CLIP

This invention relates to a surgical clip for closing aneurysms and represents an improvement over the clip structure shown in my U.S. Pat. No. 3,827,438 and in my copending application Ser. No. 061903 filed July 30, 1979 now abandoned.

An object of this invention is to provide a one-piece aneurysm clip having a spring portion which urges blades thereof toward engagement and in which a bar carried by one connecting portion of the clip overlies an opposed connecting portion to hold the blades in alignment.

A further object of this invention is to provide such a clip in which the bar includes a stop portion for preventing excessive opening of the clip.

Briefly, this invention provides a one-piece aneurysm clip formed of a metal alloy strip which includes a central portion formed to a helical spring. First connecting portions extend from ends of the helical portion. The first connecting portions normally are spaced and diverge from the helical portion. Second connecting portions extend from the first connecting portions and are offset and cross. Blade members extend from the second connecting portions and are arranged to engage in substantially flatwise relation. A bar carried by one of the second connecting portions overlies the opposed second connecting portion to hold the blade members in alignment. The bar is connected to said one of the second connecting portions by a cross piece. The cross piece is engageable by the opposed second connecting portions to limit opening movement of the blade members to prevent excessive opening movement of the blade members.

The above and other objects and features of the invention will be apparent to those skilled in the art to which this invention pertains from the following detailed description and the drawing, in which.

In the following detailed description and the drawing, like reference characters indicate like parts.

Figure 1:
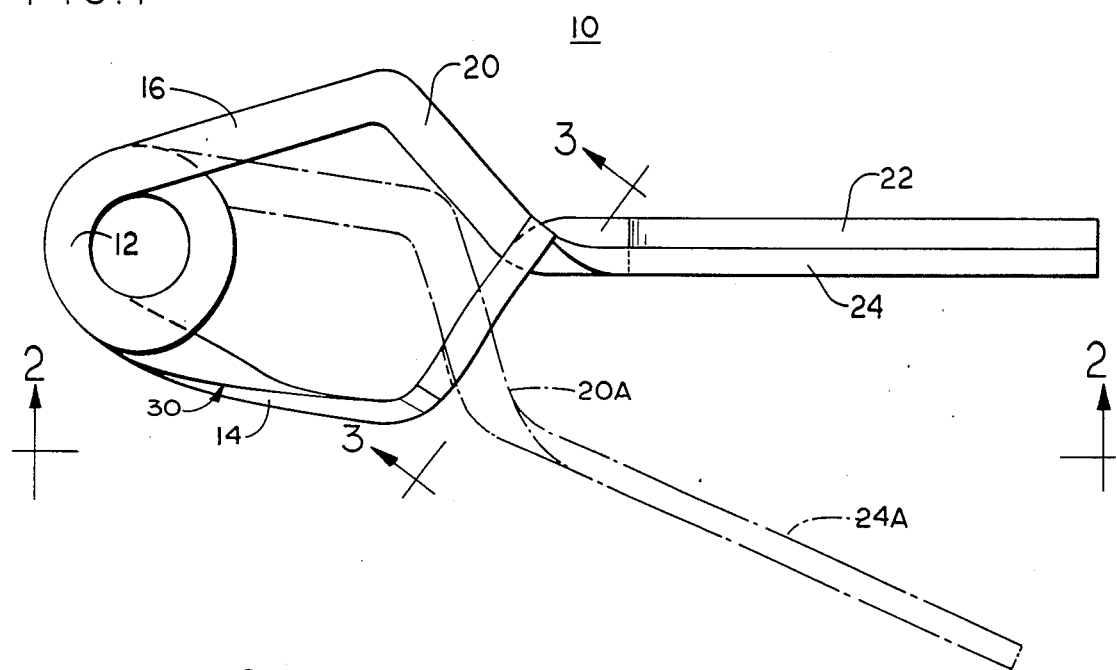
FIG. 1 is a plan view of an aneurysm clip constructed in accordance with an embodiment of this invention, one of the blades and associated connecting portions thereof being shown in open position in dot-dash lines.
Figure 2:
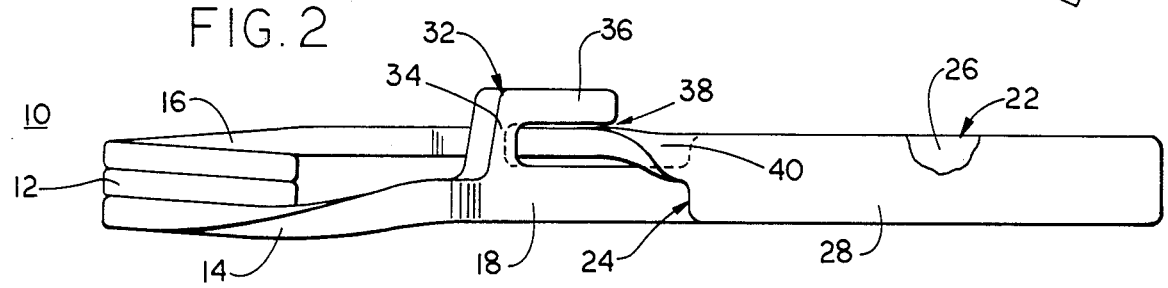
FIG. 2 is a view in side elevation of the aneurysm clip looking in the direction of the arrows 2—2 in FIG. 1.
Figure 3:
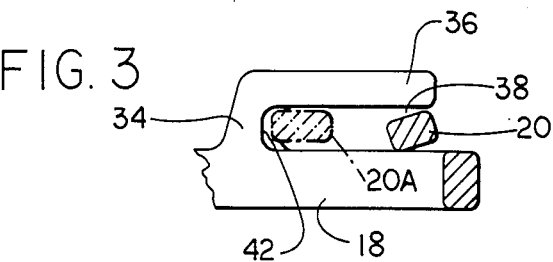
FIG. 3 is a view in section taken on the line 3—3 in FIG. 1.

In FIGS. 1–3 inclusive is shown a one-piece aneurysm clip 10 constructed in accordance with an embodiment of this invention. The clip can be formed from a ribbon of metal alloy which is resistant to corrosion or deterioration in the presence of body fluids and which is capable of forming a strong spring. A preferred material for the clip is an alloy consisting essentially of 35 percent nickel, 35 percent cobalt, 20 percent chromium and 10 percent molybdenum, all percentages being taken by weight.

The clip 10 includes a helically wound central spring section 12. The ribbon is wound with the wide sides thereof perpendicular to the axis of the helically wound section for maximum spring strength. First connecting portions 14 and 16 are integral with an extend from opposite ends of the helically wound central spring section 12. As shown in FIG. 1, the first connecting portions 14 and 16 diverge from the central spring section 12. Second connecting portions 18 and 20 are integral with and converge from outer end portions of the first connecting portions 14 and 16, respectively. Blade portions 22 and 24 are integral with and extend from outer ends of the second connecting portions 18 and 20, respectively, into position for engaging in face-to-face relation when the clip is in closed position as shown in full lines in FIG. 1. The blade portions 22 and 24 include side sections 26 and 28, respectively, so that each blade portion overlies substantially the entire other blade portion when in closed position. The first connecting portion 14 is connected to the central spring section 12 by a 90 degree turn 30 so that the first connecting portion 14, the second connecting portion 18 and the blade portion 22 are in planes parallel to the axis of the central spring section 12. A guide bar and stop member 32 is mounted on the second connecting portion 18. The guide bar and stop member 32 is of generally angle shape and includes a stop portion 34 integral with and extending substantially normally to the second connectng portion 18 and a guide bar portion 36 integral with the stop portion 34 and extending cantilever-fashion substantially parallel to the second connecting portion 18. The guide bar portion 36 is spaced from the second connecting portion 18 to form a guide slot 38 in which the second connecting portion 20 is received. The second connecting portion 20 is connected to the blade portion 24 by a 90 degree turn 40 so that the blade portion 24 is in a plane parallel to the axis of the central spring section 12.

The clip 10 can be opened to the position at which the blade 24 is shown in dot-dash lines at 24A in FIG. 1 by an appropriate tool (not shown). As the clip 10 is opened, the second connecting portion 20 advances to the position shown in dot-dash lines at 20A in FIG. 3. A face 42 of the stop portion 34 is engageable by the second connecting portion 20 to limit the opening of the clip 10.

The clip illustrated in the drawing and described above is subject to structural modification without departing from the spirit and scope of the appended claims.

Having described my invention, what I claim as new and desire to secure by letters patent is:

1. A one-piece aneurysm clip having an elongated flat ribbon body including a central helical section joining first connecting portions, wide sides of the flat ribbon body in the helical section being substantially normal to the axis of the helical section, second connecting portions extending from the first connecting portions transversely of the first connecting portions, blade portions extending from the second connecting portions, the blade portions being engageable substantially flatwise, spring action of the helical section urging the blade portions to engaged position, and a guide bar and stop member mounted on one of the second connecting portions and overlying an opposed other of the second connecting portions, the guide bar and stop member including a stop portion extending outwardly of said one of the second connecting portions and being engageable by the other of the second connecting portions to limit opening of the clip and a guide bar portion spaced from and substantially parallel to said one of the second connecting portions to hold the blade portions in alignment, there being a 90 degree turn in the ribbon between the helical section and said one of the second connecting portions so that said one of the second connecting portions is in a plane parallel to the axis of the helical section.

* * * * *